United States Patent
Medan et al.

(10) Patent No.: US 7,128,711 B2
(45) Date of Patent: Oct. 31, 2006

(54) POSITIONING SYSTEMS AND METHODS FOR GUIDED ULTRASOUND THERAPY SYSTEMS

(75) Inventors: Yoav Medan, Haifa (IL); Avner Ezion, Haifa (IL)

(73) Assignee: Insightec, Ltd. (IL)

( * ) Notice: Subject to any disclaimer, the term of this patent is extended or adjusted under 35 U.S.C. 154(b) by 168 days.

(21) Appl. No.: 10/106,562

(22) Filed: Mar. 25, 2002

(65) Prior Publication Data

US 2003/0181806 A1 Sep. 25, 2003

(51) Int. Cl.
*A61B 8/12* (2006.01)
(52) U.S. Cl. ............... 600/439; 600/437; 600/444; 600/445; 600/459; 601/2; 601/3
(58) Field of Classification Search ............ 601/2, 601/3, 4; 600/437, 439, 410, 411, 407, 421; 324/307, 309, 316
See application file for complete search history.

(56) References Cited

U.S. PATENT DOCUMENTS

| | | | |
|---|---|---|---|
| 5,443,068 A | * | 8/1995 | Cline et al. ............... 600/411 |
| 5,526,814 A | | 6/1996 | Cline et al. |
| 5,553,618 A | * | 9/1996 | Suzuki et al. ............. 600/411 |
| 5,583,901 A | | 12/1996 | Reiter et al. |
| 5,897,495 A | * | 4/1999 | Aida et al. ................ 600/411 |
| 5,944,663 A | * | 8/1999 | Kuth et al. ................ 600/411 |
| 6,122,538 A | * | 9/2000 | Sliwa et al. ............... 600/407 |
| 6,546,279 B1 | * | 4/2003 | Bova et al. ................ 600/429 |
| 6,780,153 B1 | * | 8/2004 | Angelsen et al. .......... 600/444 |

FOREIGN PATENT DOCUMENTS

| | | |
|---|---|---|
| DE | 195 12 956 A1 | 10/1996 |
| DE | 100 32 982 A1 | 2/2002 |

* cited by examiner

*Primary Examiner*—Brian L. Casler
*Assistant Examiner*—William C Jung
(74) *Attorney, Agent, or Firm*—Vista IP Law Group LLP

(57) ABSTRACT

Systems and methods are provided for positioning a therapy device, such as an ultrasound transducer, using a tilt sensor carried by the transducer and a positioner coupled to the transducer. The positioner provides roll and pitch control as well as translating the transducer in lateral and longitudinal directions. A processor receives signals from the tilt sensor corresponding to the actual rotational orientation of the transducer and controls the positioner to adjust the orientation of the therapy device until a desired position is achieved.

26 Claims, 3 Drawing Sheets

POSITIONING SYSTEMS AND METHODS FOR GUIDED ULTRASOUND THERAPY SYSTEMS

FIELD OF THE INVENTION

The present invention pertains to systems and methods for performing therapeutic procedures using focused ultrasound, and, more particularly, to systems and methods for positioning therapeutic or diagnostic devices, such as a focused ultrasonic transducer.

BACKGROUND

Focused ultrasonic therapy uses localized heating to destroy tumors or other tissue anomalies. Heating tissue beyond a critical temperature for a period of time causes the destruction of tissue (necrosis). Using Magnetic Resonance Imaging (MRI) guidance to guide the focal point of an ultrasonic therapy device is well known. For instance, U.S. Pat. Nos. 5,443,068, 5,275,165, and 5,247,935, each describes using an ultrasonic transducer guided by an MRI system to selectively destroy tissue.

In order to accurately position a focused ultrasonic therapy device, a positioner may be employed, which should provide repeatedly predictable control of the ultrasonic transducer. For example, tumors that are small or have irregular shapes require exact positioning of the ultrasonic transducer in order to destroy only the intended tissue while leaving the surrounding healthy tissue undamaged.

Known positioners, such as those described in U.S. Pat. Nos. 5,247,935 and 5,275,165, use hydraulic mechanisms to position an ultrasonic transducer beneath a patient. These systems have inherent reliability and accuracy problems due to the hydraulic positioners, which may experience motor backlash, degrading the accuracy of the positioner.

The need to accurately position an ultrasonic transducer for use in selective tissue necrosis presents additional problems when the transducer is used in combination with a Magnetic Resonance Imaging (MRI) guidance system. MRI systems employ large magnets for creating a homogenous magnetic field, and gradient coils for altering the magnetic field in a uniform manner in time and/or space to create magnetic field gradients. MRI systems also employ radio frequency (RF) coils for applying an RF field to the tissue that is to be imaged, causing the tissue to resonate and create an MR response signal. The MR response signal is then used to construct an image of the tissue that may be displayed, printed, and/or stored for later use and analysis. The degree of homogeneity of the magnetic field and the linearity of the magnetic field gradient over space and time are important in creating a clear undistorted image. Any interference with the RF field may reduce the quality of the image. The best and most consistent imaging typically occurs when surgical equipment or other objects do not interfere with the magnetic and RF fields created by the MRI system.

For example, equipment that is constructed from ferromagnetic materials should not be used near an MRI system since the large magnetic fields generated by the MRI system may physically attract the magnetic equipment. Furthermore, conductive materials may disturb and distort the radio frequency electromagnetic fields necessary for resonance imaging. Other problems may occur with materials that produce eddy currents when placed in a time-varying magnetic field. The eddy currents in these materials, usually electrical conductors, may create their own magnetic field that may interfere with the fields used for magnetic resonance imaging. Therefore, materials that exhibit good conductivity, such as aluminum and copper, should not be used within a time-varying magnetic field.

For these reasons, motors of positioners used to move the transducer may be placed at a significant distance from the ultrasonic transducer and MRI system, i.e., outside the MRI imaging space. Such positioners therefore require long drive shafts and/or multiple joints, which may increase the physical footprint of the positioner. This arrangement also may cause inaccuracies in determining the actual position of the transducer due to mechanical freedom and elasticity of the transmission components extending from the motor to the ultrasonic transducer.

For example, U.S. Pat. No. 5,443,068 describes an MRI guided ultrasonic therapy system that uses threaded shafts attached to screw drives through universal joints in order to position a transducer in three orthogonal linear dimensions. The screw drives, and particularly the universal joints, used in this system compound motor backlash problems and therefore may limit the accuracy of the system. Furthermore, the motor drives may be formed from magnetic material and, therefore, are located away from the imaging space to eliminate interference with the MRI system. Therefore, this system may introduce reliability and accuracy problems explained above.

Accordingly, positioning systems for accurately positioning a therapeutic or diagnostic device, such as an ultrasound transducer, would be useful.

SUMMARY OF THE INVENTION

The present invention is directed to systems and methods for performing therapeutic and/or diagnostic procedures using focused ultrasound, and, more particularly, to systems and methods for positioning therapeutic or diagnostic devices, such as an ultrasonic transducer.

According to one aspect of the present invention, a sensor may be physically connected to a therapeutic and/or diagnostic device, e.g., an ultrasound transducer, to measure a position of the device. Based on the position measurement, a processor may direct a positioner to adjust a position of the device, e.g., to direct energy from the device towards a target tissue region, e.g., a benign or malignant tumor, within a patient. The position measurement may be a measurement of a location or an orientation of the therapeutic device.

In accordance with another aspect of the present invention, a system is provided for directing acoustic energy towards a patient during a therapeutic or diagnostic procedure that includes an acoustic transducer, a positioner connected to the transducer for adjusting a position of the transducer, and a sensor carried by the transducer for measuring a position of the transducer. A processor is coupled to the sensor for receiving signals from the sensor related to the position of the transducer. In addition, the processor may be coupled to the positioner for directing the positioner to adjust the position of the therapy based at least in part on the signals received from the sensor.

In accordance with still another aspect of the present invention, a method is provided for positioning an acoustic transducer or other therapeutic or diagnostic device. A position, e.g., one or more tilt angles, of the transducer may be adjusted towards a desired position within a reference frame, e.g., based upon an input. An actual position of the transducer may be measured within the reference frame using a device carried by the transducer, e.g., using a tilt sensor to measure one or more tilt angles of the transducer. The actual position of the transducer may be compared with the desired position, e.g., by comparing signals from the tilt sensor with the input. If the actual position does not substantially match the desired position, the position of the transducer may be adjusted further, and the process repeated. Thus, systems and methods in accordance with the present invention may provide an iterative process for accurately positioning an acoustic transducer during a medical procedure.

Other and further aspects and features of the invention will be evident from reading the following detailed description of the drawings, which is intended to illustrate, not limit, the invention.

BRIEF DESCRIPTION OF THE DRAWINGS

Preferred embodiments of the present invention are illustrated by way of example, and not by way of limitation, in the figures of the accompanying drawings, in which like reference numerals refer to like components, and in which.

DETAILED DESCRIPTION OF THE PREFERRED EMBODIMENTS

Figure 1:
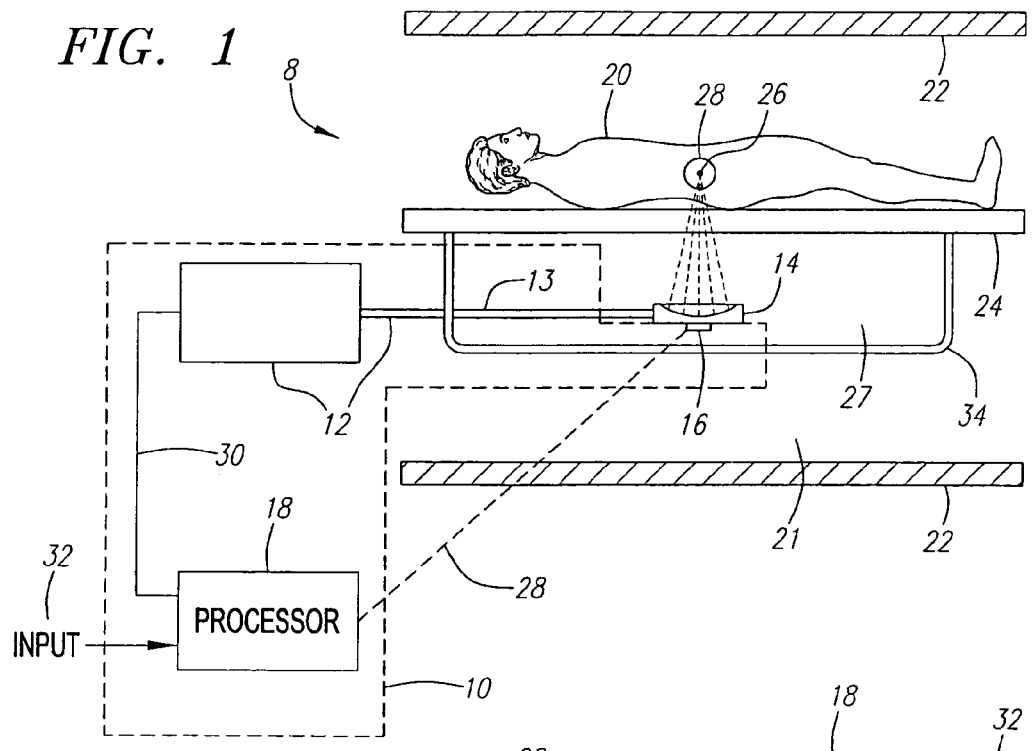
FIG. 1 illustrates an embodiment of a focused ultrasound system, including an ultrasound transducer, a system for positioning the transducer, and an MRI system, in accordance with the present invention.

Turning to the drawings, FIG. 1 illustrates an exemplary embodiment of a focused ultrasound system 8 including an ultrasonic transducer 14, a positioning system 10 for positioning the transducer 14, and a magnetic resonance imaging ("MRI") system 22. The positioning system 10 includes a positioner 12 coupled to the transducer 14, a sensor 16 carried by the transducer 14, and a processor 18 coupled to the positioner 12 and sensor 16, as explained further below.

The transducer 14 may be mounted within a chamber 27 filled with degassed water or similar acoustically transmitting fluid. The chamber 27 may be located within a table 34 upon which a patient 20 may be disposed, or within a fluid-filled bag mounted on a movable arm that may be placed against a patient's body (not shown). The contact surface of the chamber 27, e.g., the top 24 of the table 34, generally includes a flexible membrane (not shown) that is substantially transparent to ultrasound, such as mylar, polyvinyl chloride (PVC), or other suitable plastic material. Optionally, a fluid-filled bag (not shown) may be provided on the membrane that may conform easily to the contours of the patient 20 disposed on the table, thereby acoustically coupling the patient 20 to the transducer 14 within the chamber 27. In addition or alternatively, acoustic gel, water, or other fluid may be provided between the patient 20 and the membrane to facilitate further acoustic coupling between the transducer 14 and the patient 20.

In addition, the transducer 14 may be used in conjunction with an imaging system. For example, the table 34 may be positioned within an imaging volume 21 of an MRI system 22, such as that disclosed in U.S. Pat. Nos. 5,247,935, 5,291,890, 5,368,031, 5,368,032, 5,443,068 issued to Cline et al., and U.S. Pat. Nos. 5,307,812, 5,323,779, 5,327,884 issued to Hardy et al., the disclosures of which are expressly incorporated herein by reference.

In order to position the transducer 14, e.g., to direct a focal zone 26 of the transducer 14 towards a target tissue region 28 within the patient 20, the positioner 12 may move the transducer 14 in one or more degrees of freedom. For example, the transducer 14 may be rotated, or translated relative to the patient 20. The positioner 12 is typically distanced away from the MRI system 22, e.g., outside the imaging volume 21 in order to minimize interference. Known positioners, which may include one or more motors, drive shafts, joints, and the like, have been described in U.S. Pat. Nos. 5,443,068, 5,275,165, and 5,247,935, and in the U.S. patent application Ser. No. 09/628,964, the disclosures of which are expressly incorporated by reference herein.

Figure 2:
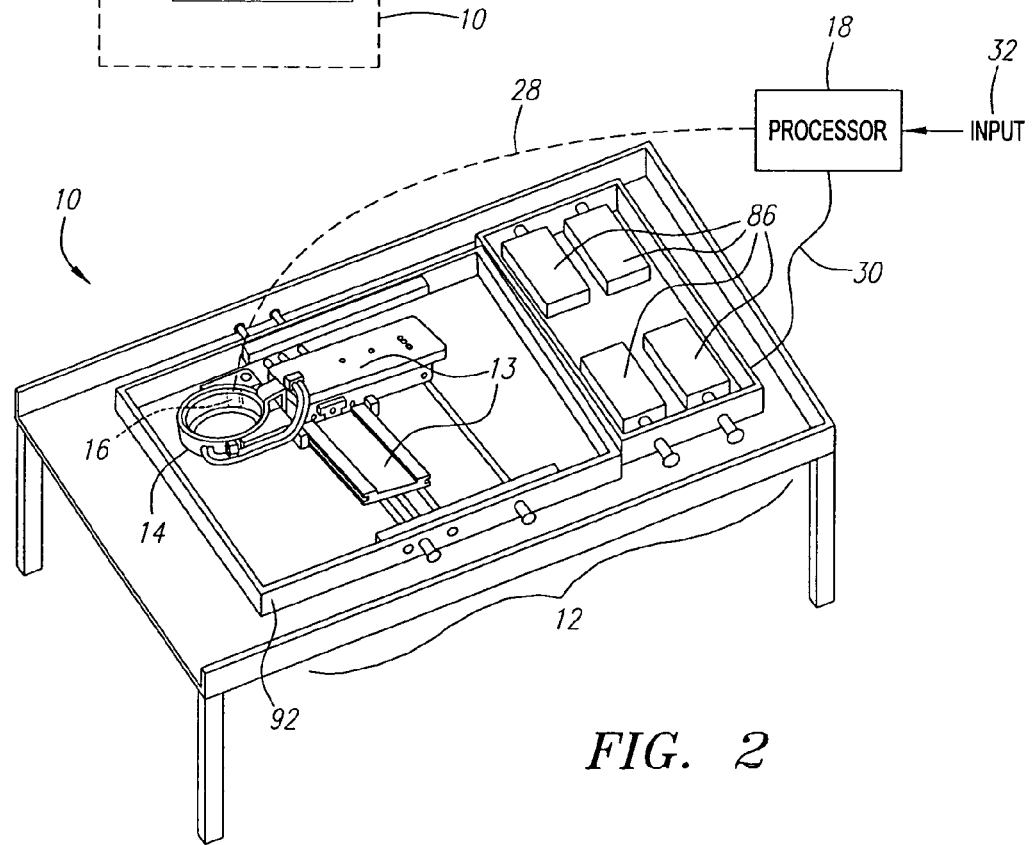
FIG. 2 is a preferred embodiment of a system for positioning the transducer of the system shown in FIG. 1.

"FIG. 2 illustrates a system 10 for positioning the transducer 14 according to a preferred embodiment. As used here, positioning includes translating or moving the transducer 14 to a new location in space, as well as rotating or tilting the transducer 14 about an axis to achieve a new orientation of the transducer 14. The positioner 12 shown in FIG. 2 may provide roll and pitch control of the transducer 14, as well as lateral and longitudinal control, as explained further below. The positioner 12 may include piezoelectric vibrational motors 86 that may operate within the field of an MRI system without interfering substantially with its operation, such as those described in U.S. patent application Ser. No. 09/628,964, filed Jul. 31, 2000, which is incorporated by reference herein. The motors 86 may provide a braking force to the drive shafts (not shown) while de-energized and thus aid in preventing motor slippage or backlash. The positioner 12 may also include a set of encoders (not shown), which are described in the U.S. patent application Ser. No. 09/628,964, coupled to the positioning motors 86 to control the position of the transducer 14."

Figure 3:
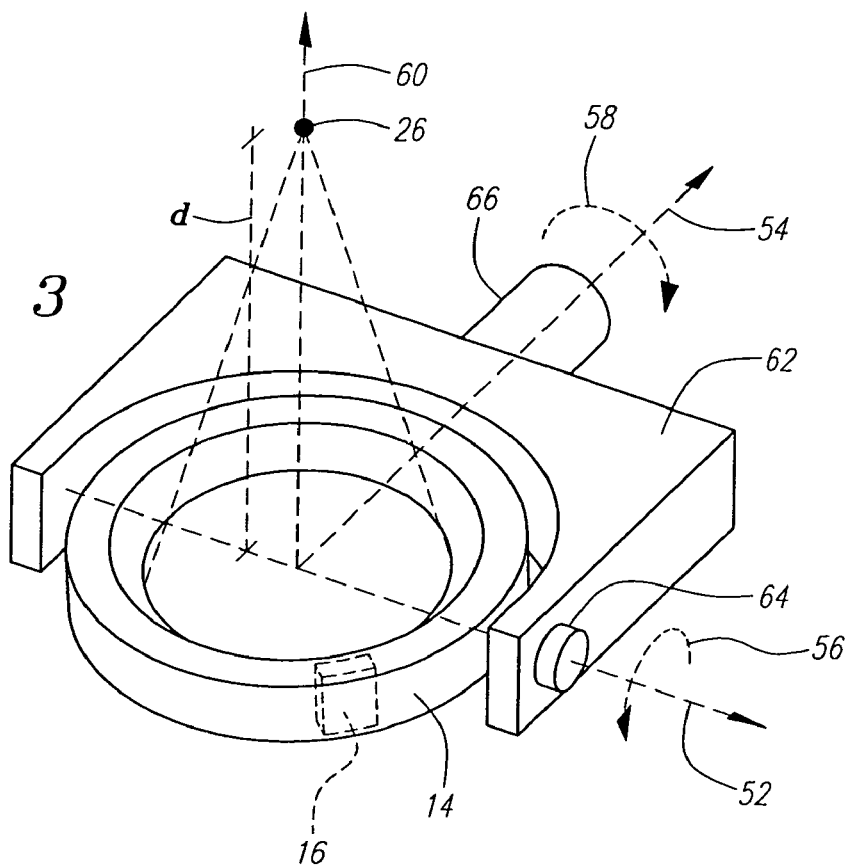
FIG. 3 is a perspective view of an exemplary embodiment of an ultrasonic transducer including a sensor for use with the system of FIGS. 1 and 2.

Turning to FIG. 3, an exemplary embodiment of an ultrasonic transducer 14 for use with the systems of FIGS. 1 and 2 is shown. The transducer 14 may include a single piezoelectric transducer element, or may include multiple piezoelectric elements (not shown) together providing a transducer array. In one embodiment, the transducer 14 may have a concave or bowl shape, such as a "spherical cap" shape, i.e., having a substantially constant radius of curvature such that the transducer 14 has an inside surface defining a portion of a sphere. Alternatively, the transducer 14 may have a substantially flat configuration (not shown), and/or may include an outer perimeter that is generally, but not necessarily, circular. The transducer 14 may be divided into any desired number of rings and/or sectors (not shown). In one embodiment, the transducer 14 may have an outer diameter of between about eight and twelve centimeters (8–12 cm), a radius of curvature between about eight and sixteen centimeters (8–16 cm), and may include between ten and thirty (10–30) rings and between four and sixteen (4–16) sectors.

In alternative embodiments, the transducer 14 may include one or more transducer elements having a variety of geometric shapes, such as hexagons, triangles, squares, and the like, and may be disposed about a central axis, preferably but not necessarily, in a substantially uniform or symmetrical configuration. The configuration of the transducer 14, however, is not important to the present invention, and any of a variety of transducers may be used, such as flat circular arrays, linear arrays, and the like. Additional information on the construction of transducers appropriate for use with the present invention may be found, for example, in co-pending application Ser. No. 09/884,206, filed Jun. 9, 2001. The disclosure of this application and any references cited therein are expressly incorporated herein by reference.

Figure 4:
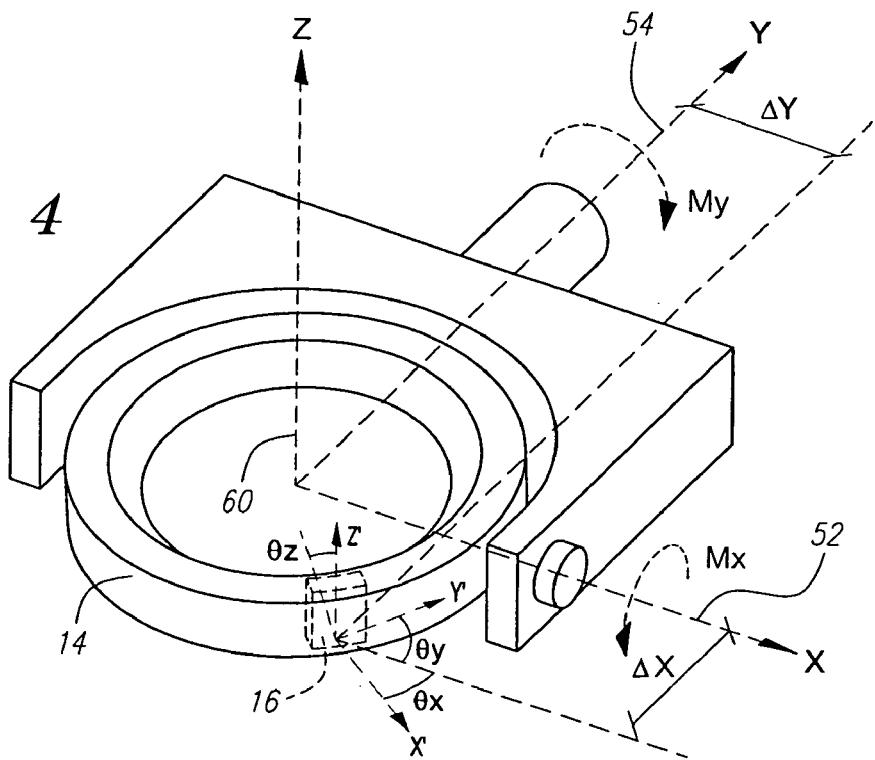
FIG. 4 is a perspective view of the transducer of FIG. 3, showing exemplary coordinate systems.

The transducer 14 may be movable within the chamber 27 (not shown, see FIG. 1), e.g., translated along a first or longitudinal axis 52, and/or along a second or transverse axis 54. The axes 52, 54 may define orthogonal coordinates (such as "X" and "Y" as shown in FIG. 4, and discussed further below) forming a plane that is substantially parallel to the top 24 of the table 34 (not shown, see FIG. 1). The transducer 14 may also be rotatable about the axis 52, as illustrated by arrow 56, showing a "pitch" motion, and/or about the axis 54, as illustrated by arrow 58, showing a "roll" motion. The focal zone 26 of the transducer 14 may also be adjustable along a Z-axis 60 (an axis substantially normal to the surface of the transducer 14 or a plane defined by axes 52, 54) electronically, as is know to those skilled in the art. Alternatively, the positioner 12 may also mechanically move the transducer 14 along an axis (not shown) that may be normal to a plane defined by axes 52, 54.

The transducer 14 may be supported by a holder or frame 62 including one or more pivotal supports 64, which may allow the transducer 14 to rotate about one of the axes 52, 54 (axis 52 shown) relative to the holder 62. The transducer holder 62, in turn, may be rotatably supported at support 66, allowing the transducer 14 to rotate about the other one of the axes 52, 54 (axis 54 shown). The support 66 may be pivotally connected to other components of the positioner 12, such as the translational mechanisms 13 shown in FIGS. 1 and 2. The translational mechanisms 13 may be movable within the chamber 27, e.g., along the axes 52, 54 for translating the transducer 14 within the plane defined by the axes 52, 54.

Thus, the holder 62 and the supports 64 and 66 may be part of the positioner 12 such that the positioner 12 may rotate the transducer 14 about the supports 64 and 66, and thereby, about the pitch and roll axes, 52 and 54, respectively. Alternatively, other frame or support structures may be provided for supporting the transducer 14, as will be appreciated by those skilled in the art, and the present invention is not limited to the exemplary embodiment shown in FIGS. 2 and 3.

Preferably, the sensor 16 is mounted internally within a portion of the transducer 14 as shown in FIG. 3. This may eliminate the need to make the sensor water proof, and may allow spare wires already provided in transducer cables (not shown) to be used to couple the sensor 16, e.g., to the processor 18 (not shown). Alternatively, the sensor 16 may also be mounted to an external surface (not shown) of the ultrasonic transducer 14. In this alternative, the sensor 16 may be provided in substantially sealed packaging, e.g., within a waterproof casing to prevent fluid surrounding the transducer 14 from damaging the sensor 16.

In either case, the sensor 16 is substantially fixed to the transducer 14 such that a rotational orientation of the sensor 16 may be correlated to a rotational orientation of the transducer 14, as explained further below. The sensor 16 is configured to measure a location or an orientation of the transducer 14 with respect to a known coordinate system, such as a coordinate system of the MRI volume. The sensor 16 may be a location sensor that measures a relative location between the transducer 14 and at least one known reference point. Location sensors, such as those that use infrared technology, are well known in the art. Alternatively or in addition, the position sensor 16 may be a tilt sensor that measures tilt angles with respect to a roll axis and/or a pitch axis of the transducer 14. Sensor 16 preferably measures tilt angle by sensing gravity field acceleration. For example, a 2-axis solid-state miniature accelerometer, available from Analog Devices Inc., Norwood, Mass., U.S., (Part Number ADXL202EB-232A), may be used for measuring tilt angles by sensing the gravity field acceleration components due to a tilt of the transducer 14.

The accelerometer chip may be made MR compliant by providing it within a case made of MR compliant materials. Furthermore, the components of the sensor 16, as well as the supporting hardware of the sensor 16, are preferably made of materials that are MR-compliant in order to reduce image artifacts. Materials that are MR-compliant include non-magnetic materials such as plastic, copper, brass, alumina, ceramic, or glass.

Returning to FIG. 1, the processor 18 may include one or more logic circuits, a microprocessor, and/or computers coupled to the sensor 16 to receive signals from the sensor 16, and to the positioner 12 for directing the positioner 12 to move the transducer 14 in a translational or rotational motion. The processor 18 may be a separate subsystem from a controller or other subsystems (not shown) used to operate the transducer 14 and/or the MRI system 22. Alternatively, the processor 18 may be included in a computer that includes hardware components and/or software modules for performing other functions of the system 8, e.g., controlling the transducer 14 and/or the MRI system 22.

A first communication path 28 allowing signals to be communicated from the sensor 16 to the processor 18 may include one or more wires coupling the sensor 16 to the processor 18. In addition or alternatively, the first communication path 28 may include an optical cable and/or a wireless transmitter for transmitting signals from the sensor 16 to the processor 18. A wireless transmitter may transmit signals, such as radio frequency, infrared, or other signals, to a receiver (not shown) coupled to the processor 18. The frequency of such radio frequency signals may be selected to minimize interference with the MRI system. Similarly, the second communication path 30, which couples the processor 18 and the positioner 12, may include one or more wires, optical cables, and/or a wireless transmitter.

The positioning system 10 may also include an interface, such as a keyboard, a mouse, and/or touch screen (not shown) for providing an input 32 to the processor 18, the positioner 12, and/or other components of the system 8, as described below.

To use the system 10, a user may enter an input 32, preferably through the interface, which may define or otherwise include a desired position of the transducer 14. As used herein, "position" may include one or both of a location in space (e.g., in one, two, or three dimensions) and an orientation (e.g., a pitch or roll angle) of the transducer 14. Preferably, the desired position of the transducer 14 includes a translation location along the axes 52 and/or 54 and/or a rotational orientation of the transducer 14 about axes 52 and/or 54.

Once the processor 18 receives an input 32 identifying a desired position of the transducer 14, the processor 18 may transmit a signal to the positioner, instructing the positioner 12 to move the transducer 14 based at least in part on the input 32 to the desired position. For example, the processor 18 may instruct the positioner 12 to move the transducer 14 based upon a calculation performed by the processor 18, e.g., a difference between the desired position and a current position of the transducer 14.

Alternatively, the positioner 12 may receive the input 32 directly and may move the transducer 14 based at least in part on the input 32. In this alternative, the input 32 (or the desired position) may be transmitted from the positioner 12 to the processor 18.

Once the positioner 12 has moved the transducer 14, the sensor 16 may measure an actual position of the transducer 14 and compare it to the desired position. For example, the processor 18 may receive one or more data signals from the sensor 16, e.g., via the first communication path 28. The processor 18 may then determine the true tilt angle based on the sensor measurement and, optionally, a set of calibration coefficients. The calibration coefficients may be associated with coordinate transformation, as is known in the art, which relates the mounting position of the sensor 16 to the coordinate system of the transducer 14. In particular, the calibration coefficients may be used to correct misalignment between the coordinate systems of the transducer 14 and the sensor 16, and to account for the geometric relation between the sensor's measurement axis and the transducer rotation axis, as discussed previously. The calibration coefficients may be initially or periodically determined using a calibration procedure, such as that discussed below.

If the true position of the transducer 14 does not match the desired position, the processor 18 may direct the positioner 12 to adjust the position of the transducer 14, for example, based on the difference between the true position and the desired position. This iterative process of obtaining the position data, determining the true position, comparing the true and desired positions, and adjusting the position of the ultrasonic transducer 14, may be repeated until the desired position associated with the user's input 32 is achieved within an acceptable tolerance level. For example, the desired tilt angle may be considered to be achieved if the true tilt angle is within a predetermined range around the desired tilt angle, such as within 0.25 degree of the desired tilt angle.

Turning to FIG. 4, movement of the transducer 14 of FIGS. 2 and 3 is shown relative to a fixed coordinate system. As shown, the roll axis 52, the pitch axis 54, and the vertical axis 60 define X, Y, and Z axes, respectively. The sensor 16 (shown in phantom), is preferably fixed to the transducer 14, and includes its own coordinate system, represented as X', Y', and Z'. In one embodiment, the coordinate system of the sensor 16 may substantially overlap the X-Y-Z coordinate system. Alternatively, internal transducer components, as well as mounting inaccuracy, may prevent precise alignment of the sensor 16 with the roll axis 106 and the pitch axis 108. As a result, alignment deviation, such as $\Delta X$ or $\Delta Y$, may exist between the X-Y-Z coordinate system and the X'-Y'-Z' coordinate system. Also, sensor 16 may be mounted with its axis, X', Y', and Z' defining angles $\theta_X$, $\theta_Y$, and $\theta_Z$, respectively, with the corresponding axis, X, Y, and Z, of the transducer 14. Therefore, before operating the system, the sensor 16 may be calibrated to account for the geometric relation between the sensor's measurement axis, X', Y', and Z', and the transducer axis, X, Y, and Z. Furthermore, since sensors that measure tilt angles may measure tilt angles with respect to gravity vectors, rather than with respect to the transducer axis, calibration may be needed to account for this as well.

Figure 5:
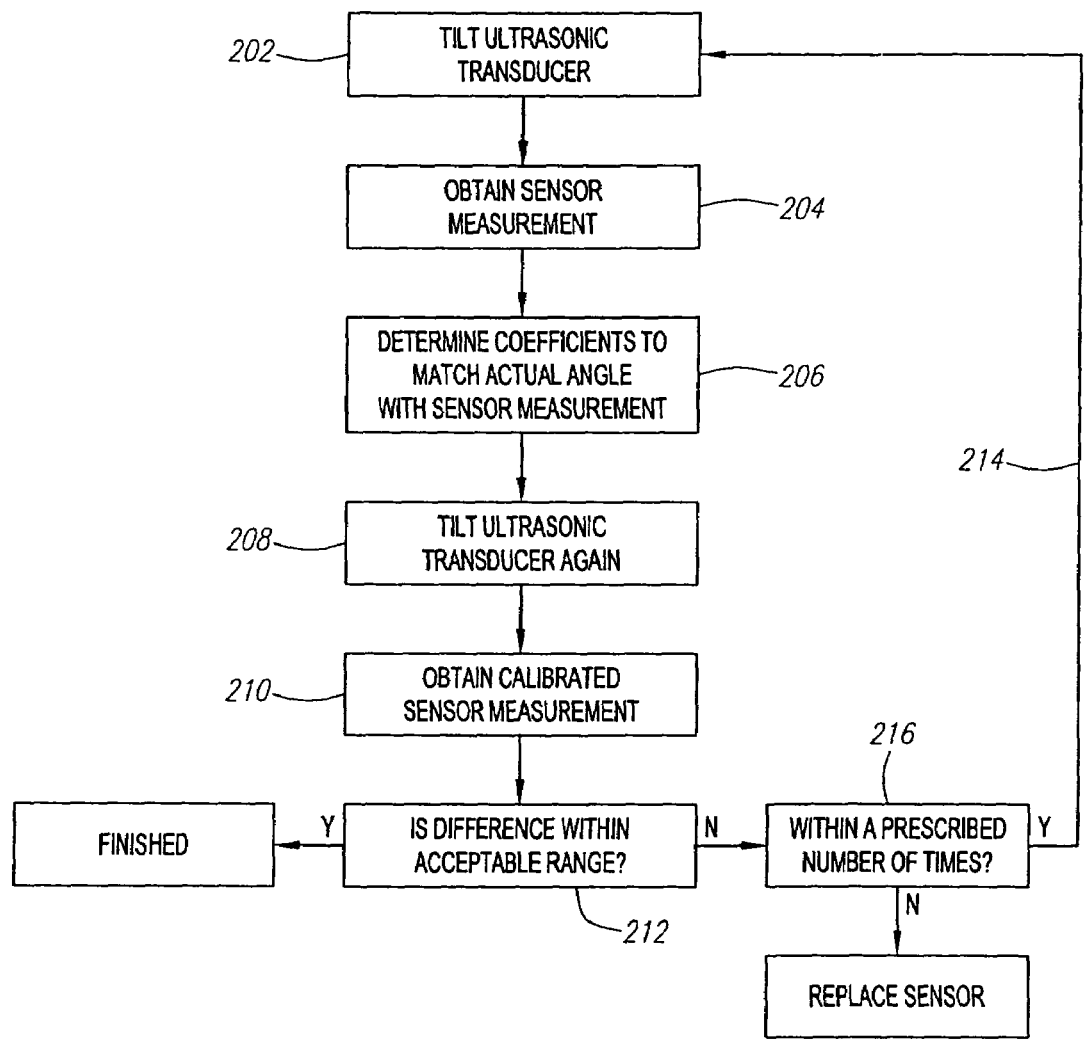
FIG. 5 is a flow chart illustrating a method for calibrating a tilt sensor carried by an ultrasonic transducer, in accordance with the present invention.

FIG. 5 is a flowchart illustrating a method 200 for calibrating a tilt sensor 16 mounted to a transducer 14 (not shown, see FIGS. 3 and 4), such as that described above. In step 202, the transducer 14 may be tilted about an axis, such as a roll axis or a pitch axis, to a plurality of angles within a range of prescribed angles. The transducer 14 may be tilted over a range that exceeds a range of angles likely to be used during an actual operation of the transducer 14. This may ensure that a complete operational range of angles is calibrated. For example, range of prescribed angles may range from $-30°$ to $+30°$ with respect to the vertical axis of the transducer 14.

In step 204, a sensor signal is obtained with the transducer 14 positioned at each of the prescribed angles. Then, in step 206, coefficients associated with coordinate transformation may be computed, that best match the sensor measurements with the corresponding prescribed angles. The coefficients may account for any imperfect mounting of the sensor, as discussed previously.

In step 208, the transducer 14 is again tilted about the same axis within a range of prescribed angles. The range of the prescribed angles in step 208 may be the same as or preferably different from the range of prescribed angles in step 202. Again, as discussed previously, the transducer 14 may be tilted within a range that exceeds the range of angles used during actual operation of the transducer 14. In step 210, sensor measurements are obtained at each of the prescribed angles generated in step 208. The sensor measurements are then calibrated using the coefficients obtained in step 206 to determine the actual tilt angle of the transducer 14 at each of the prescribed angles.

In step 212, each of the actual tilt angles, as determined by the calibrated sensor measurements in step 210, may be compared with each of the prescribed angles generated in step 208. If the difference is within an acceptable range, preferably within 0.3 degree, then the calibration procedure is finished.

If the difference between each of the calibrated sensor measurements in step 210 and each of the prescribed angles is not within an acceptable range, the sensor may be re-calibrated. Preferably, there should be a prescribed number of times for repeating calibration of the sensor 16. In step 216, it is determined whether the prescribed number of times is met. If the sensor has only been calibrated once, for example, then the calibration procedure may be repeated starting at step 202, as shown by the arrow 214 defining a process loop. After a prescribed number of calibrations, if the sensor measurements cannot be calibrated to match the prescribed angles within an acceptable range of error, the sensor 16 may be replaced, as shown in step 218.

If the sensor is configured to measure tilt angles about two axes or more, then the calibration procedure described above may be performed for each axis. In this case, the coefficients may account for sensor readings in all axes. In addition, if more than one sensor is mounted to the ultrasonic transducer, the calibration procedure described above needs to be performed for each of the sensors. It should be noted that although a calibration method for a tilt sensor is described above, the same concept also applies to a calibration method for a position sensor that measures a location of the ultrasonic transducer.

Although the embodiments above have been described in reference to ultrasonic transducer used in conjunction with a MRI system, the scope of the invention is not so limited. The present invention also applies to other imaging modalities such as computed tomography and other medical devices that require precise positioning. For example, laser devices that are machine-coordinated or medical devices for cutting biological tissue, such as oscillation knives, may use the system described herein to ensure that the devices are positioned and aimed correctly at the target tissue. This ensures proper treatment and prevents injury to the patient.

Thus, although different embodiments have been shown and described, it would be apparent to those skilled in the art that many changes and modifications may be made thereunto without the departing from the scope of the invention, which is defined by the following claims and their equivalents.

What is claimed is:

1. A system for directing therapeutic acoustic energy to a target tissue region in a body of a patient during a therapeutic or diagnostic procedure, comprising:
   an acoustic transducer positionable outside of the patient's body for directing therapeutic acoustic energy emitted by the transducer to the target tissue region, the transducer laterally translatable and capable of at least one of pitch motion and roll motion;
   a positioner connected to the transducer for adjusting a position of the transducer, the position being both a location and an orientation of the transducer;
   a sensor fixed on the transducer such that a rotational orientation of the sensor is correlated to a rotational orientation of the transducer, the sensor adapted for measuring the position of the transducer, wherein the sensor is a tilt sensor, the tilt sensor generating signals related to at least one of a roll angle and a pitch angle of the transducer relative to one or more axes; and
   a processor coupled to the sensor for receiving signals from the sensor related to the measured position of the transducer, the processor coupled to the positioner for directing the positioner to adjust the position of the transducer during the procedure based at least in part on the signals received from the sensor.

2. The system of claim 1, wherein the tilt sensor generates signals related to a roll angle of the transducer about a first horizontal axis, and a pitch angle of the transducer about a second horizontal axis that is orthogonal to the first horizontal axis.

3. The system of claim 1, wherein the positioner comprises a support for rotating the transducer about the one or more axes.

4. The system of claim 1, wherein the sensor is a location sensor, and where the system further comprises an apparatus for detecting the location sensor within a region of space.

5. The system of claim 4, wherein the apparatus for detecting the location sensor comprises an MRI system configured for detecting a position of the location sensor within an MR imaging field of the MRI system.

6. The system of claim 1, wherein the sensor comprises an accelerometer.

7. The system of claim 1, wherein the sensor is contained within non-magnetic packaging.

8. The system of claim 1, wherein the positioner comprises one or more motors coupled to the transducer for at least one of translating the transducer within a plane and rotating the transducer about an axis.

9. The system of claim 8, wherein each of the one or more motors comprises:
   a drive shaft coupled to the transducer; and
   a piezoelectric element coupled to the drive shaft for rotating the drive shaft.

10. The system of claim 1, further comprising:
    a MRI system comprising an imaging volume, wherein the transducer is disposed within the imaging volume, and wherein the positioner is coupled to the transducer for adjusting a position of the transducer within the imaging volume.

11. The system of claim 1, wherein the sensor repeats iterations of measuring the position of the acoustic transducer and the positioner repeats adjusting the position of the acoustic transducer during the procedure until the acoustic transducer is placed in a desired position.

12. The system of claim 1, wherein the acoustic transducer is laterally translatable and capable of both pitch motion and roll motion.

13. The system of claim 1, wherein the sensor is mounted internally within the acoustic transducer.

14. A therapeutic system, comprising:
    a therapy device positionable outside of a body of a patient for directing therapeutic energy emitted by the therapy device to a target tissue region within the patient's body, the therapy device laterally translatable and capable of at least one of pitch motion and roll motion;
    a positioner connected to the therapy device for adjusting a position of the therapy device, the position being both a location and an orientation of the therapy device;
    a sensor fixed on the therapy device such that a rotational orientation of the sensor is correlated to a rotational orientation of the therapy device, the sensor adapted for measuring the position of the therapy device, wherein the sensor is a tilt sensor, the tilt sensor generating signals related to at least one of a roll angle and a pitch angle of the transducer relative to one or more axes; and
    a processor coupled to the sensor and the positioner, the processor configured to control operation of the positioner during a therapeutic procedure based at least in part on a measured position of the therapy device by the sensor.

15. The system of claim 14, wherein the therapy device comprises an ultrasonic transducer, and the sensor comprises an accelerometer mounted to the transducer for measuring a tilt angle of the transducer.

16. The system of claim 14, wherein the sensor repeats iterations of measuring the position of the therapy device and the positioner repeats adjusting the position of the therapy device during the therapeutic procedure until the therapy device is placed in a desired position.

17. The system of claim 14, wherein the therapy device is laterally translatable and capable of both pitch motion and roll motion.

18. The system of claim 14, wherein the sensor is mounted internally within the therapy device.

19. A method for positioning a therapeutic or diagnostic device during a therapeutic or diagnostic procedure, comprising:
    adjusting a position of the device towards a desired position outside a body of a patient within a reference frame, the device being laterally translatable and capable of at least one of pitch motion and roll motion, and the position being both a location and an orientation of the device;
    measuring an actual position of the device within the reference frame using a sensor fixed on the device so that a rotational orientation of the sensor is correlated to a rotational orientation of the device, wherein the sensor is a tilt sensor, the tilt sensor generating signals related to at least one of a roll angle and a pitch angle of the transducer relative to one or more axes;
    comparing the actual position with the desired position; and
    during the therapeutic or diagnostic procedure, actuating a positioner to further adjust the position of the device based on a result of comparing the actual position with the desired position.

20. The method of claim 19, wherein the actuating is performed based upon a difference between the actual position and the desired position.

21. The method of claim 19, wherein the device comprises an ultrasonic transducer.

22. The method of claim 19, wherein the sensor carried by the device is a tilt sensor, and wherein the measuring step comprises measuring an actual rotational orientation of the device with the tilt sensor.

23. The method of claim 22, wherein the positioner is actuated to adjust a rotational orientation of the device.

24. The method of claim 19, wherein the device is disposed within an imaging field of an MRI system, and wherein the measuring step comprises detecting a position of the sensor carried by the device to determine an actual position of the device.

25. The system of claim 19, wherein iterations of measuring, comparing and adjusting are repeated during the therapeutic or diagnostic procedure until the device is placed in a desired position.

26. The method of claim 19, the step of measuring comprising measuring the actual position of the device using a sensor that is mounted internally within the device.

* * * * *